United States Patent [19]
Gibbs

[11] Patent Number: 6,106,811
[45] Date of Patent: Aug. 22, 2000

[54] ORAL CARE COMPOSITION

[75] Inventor: Christopher David Gibbs, Bebington Wirral, United Kingdom

[73] Assignee: Chesebrough-Pond's USA, Co., division of Conopco, Inc., Greenwich, Conn.

[21] Appl. No.: 09/211,832

[22] Filed: Dec. 15, 1998

[30] Foreign Application Priority Data

Dec. 18, 1997 [EP] European Pat. Off. ............. 97310400

[51] Int. Cl.[7] ................................ A61K 7/16; A61K 7/18
[52] U.S. Cl. ................................................ 424/52; 424/49
[58] Field of Search .................................................. 424/52

[56] References Cited

U.S. PATENT DOCUMENTS

| | | | |
|---|---|---|---|
| 3,119,743 | 1/1964 | Ericsson | 167/93 |
| 3,966,863 | 6/1976 | Forward et al. | 424/52 |
| 4,296,696 | 10/1981 | Pierce | 424/52 |
| 4,661,341 | 4/1987 | Benedict et al. | 424/49 |
| 4,840,985 | 6/1989 | Gonnet et al. | 524/425 |
| 4,892,725 | 1/1990 | Amjad | 424/52 |
| 5,076,846 | 12/1991 | Buri et al. | 106/401 |
| 5,397,845 | 3/1995 | Rebre et al. | 525/301 |
| 5,412,037 | 5/1995 | Rebre et al. | 525/301 |
| 5,721,295 | 2/1998 | Bruggemann et al. | 542/44 |
| 5,728,742 | 3/1998 | Staples et al. | 521/57 |
| 5,856,410 | 1/1999 | Carrico et al. | 525/362 |

FOREIGN PATENT DOCUMENTS

| | | |
|---|---|---|
| 0 174 840 | 3/1986 | European Pat. Off. . |
| 73.46581 | 12/1973 | France . |
| 907417 | 10/1962 | United Kingdom . |
| 1 476 063 | 6/1977 | United Kingdom . |
| 2 227 660 | 8/1990 | United Kingdom . |
| 96/03108 | 2/1996 | WIPO . |

*Primary Examiner*—Shep K. Rose
*Attorney, Agent, or Firm*—Milton L. Honig

[57] ABSTRACT

The invention provides a oral care composition with particular calcium carbonate as abrasive cleaning agent, and a fluorine-providing compound as anti-caries agent. The loss of available fluorine, caused by interaction between the calcium carbonate and the fluorine-providing compound is reduced by inclusion in the oral care composition of fully neutralized polyacrylic acid.

7 Claims, No Drawings

ORAL CARE COMPOSITION

BACKGROUND OF THE INVENTION

1. Field of the Invention

The present invention relates to an oral care composition which comprises particulate calcium carbonate as the main or major abrasive cleaning agent.

2. The Related Art

Particulate calcium carbonate is a well-known abrasive cleaning agent in oral care compositions such as toothpastes, and toothpastes with this abrasive cleaning agents have found their way to the market place. While this abrasive cleaning agent is an acceptable abrasive cleaning agent in terms of its abrasivity, it suffers from a major drawback in that it is incompatible with fluorine-providing active ingredients in toothpastes, such as alkalimetal fluorides, which are commonly incorporated into toothpastes to provide for an anti-caries benefit.

This problem was already recognised a long time ago, and in GB-A-907,417 (Ericsson) it was proposed to overcome this drawback by using an alkalimetal monofluorophosphate instead of an alkalimetal fluoride as anti-caries agent.

In FR-A-2,251,309 (Beecham) it was proposed to use a mixture of an alkalimetal fluoride and an alkalimetal monofluorophosphate to overcome the inactivation of the fluoride by the calcium carbonate. However, while such systems can indeed result in less inactivation of the fluorine-providing anti-caries agent by the calcium carbonate, there is frequently still too much loss of the active fluorine to provide for an acceptable, efficacious anti-caries benefit.

SUMMARY OF THE INVENTION

It has now been found that the inclusion, in an oral care composition which contains particulate calcium carbonate as the main or major abrasive cleaning agent, and a fluorine-providing anti-caries agent, of a fully neutralized polyacrylate, significantly improves the compatibility of the calcium carbonate and the fluorine-providing agent, reducing the inactivation and consequently reducing the loss of available active fluorine.

DETAILED DESCRIPTION

In this respect it is observed, that in GB-A-1,476,063 (Boots) it is stated that toothpastes which contain calcium carbonate and an anionic binding agent such as sodium carboxy methyl cellulose, alginic acid, xanthan gums, carragheenin, and Carbopol® can suffer from storage stability problems, e.g. can become lumpy on cooling and/or ageing. The trademark "Carbopol" covers both polyacrylic homopolymers as well as copolymers. This storage stability is proposed to be overcome by the inclusion of an aluminosilicate according to this GB-A-1,476,063.

We have found that the inclusion of a fully neutralized polyacrylate does not cause any storage stability problem to any significant degree, thus obviating the need to use an aluminosilicate.

In ZA-A-86/0599 (Blendax) toothpastes are described which contain calcium carbonate as abrasive cleaning agent. The pH of these toothpastes is adjusted by addition of an acid to pH 7.5–8.5 to provide for a reservoir of calcium ions to effect remineralisation of tooth enamel. These toothpastes can, inter alia, comprise a thickening agent such as alkali salts of polyacrylic acid. The oral care compositions of the present invention, however, have a pH of above 8.5 and do not contain an acid, to avoid undesirable interaction between free calcium ions and the fluorine-providing anti-caries agent.

The fully neutralized polyacrylate, used in the present invention, is a polyacrylic acid which has been fully neutralized with a suitable alkalimetal-, ammonium-, or (alkylol) amine compound, such as sodium- and potassium hydroxide or- carbonate, ammonia, triethanolamine and the like. A preferred fully neutralized polyacrylate salt is the sodium salt. The polyacrylic acid is a homopolymer of acrylic acid, and has a molecular weight of between 1000 and 250,000, preferably between 2500 and 100,000, and particularly preferably between 4000 and 70,000. A particularly preferred fully neutralized polyacrylate is the sodium salt of polyacrylic acid, the latter having a molecular weight of 8000. This product is commercially available from BASF, under the tradename Sokalan PA 30 CL.

The fully neutralized polyacrylate is used in the oral care compositions of the invention in an amount, ranging from 0.05–5% by weight of the composition, usually from 0.1–3% by weight of the composition. Naturally, mixtures of the fully neutralized polyacrylates may also be used.

Although the fully neutralized polyacrylate can be formed in situ in the final oral care composition by providing therein of a sufficient amount of an alkaline material to fully neutralize the polyacrylic acid, this is not a preferred embodiment of the invention as this in situ neutralization may be difficult to control without negatively affecting other ingredients of the composition. The fully neutralized polyacrylate is preferably incorporated into the final oral care composition as such, i.e. after it has been separately neutralized.

The particulate calcium carbonate abrasive cleaning agent, used in the present invention, can be any suitable type of calcium carbonate, known in the art for inclusion in oral care compositions. It can be of natural origin, such as aragonites or calcites, e.g. finely ground marble, dolomite etc, or it can be of synthetic origin, e.g. finely precipitated calcium carbonate. It usually has an average particle size of between 1–60 $\mu$m, usually between 1–40 $\mu$m. The amount of the particulate calcium carbonate, used in the present invention, ranges from 10–60% by weight, preferably 20–50% by weight, and particularly preferably from 25–45% by weight of the oral care composition.

The fluorine-providing anti-caries agents, used in the present invention, are alkalimetal fluorides and/or alkalimetal monofluorophosphates, the latter being the preferred ones. They are usually used in amounts, sufficient to provide 50–1500 ppm available fluorine.

The oral care compositions can be formulated in any suitable application form, such as gels, toothpowders and toothpastes. They may be formulated into a single formulation or they may be formulated for multi compartment containers into different formulations, e.g. one containing the calcium carbonate and ingredients compatible therewith, and another containing the remaining ingredients.

The oral care compositions of the present invention may furthermore comprise optional, conventional ingredients such as pharmaceutically acceptable carriers like starch, sucrose, water or water/alcohol systems etc. Small amounts of surfactants may also be included, such as anionic, nonionic, cationic and amphoteric surfactants. When formulated into a dentifrice, such formulation may contain all the usual dentifrice ingredients.

Thus, they may comprise additional particulate abrasive materials such as silicas, aluminas, dicalciumphosphates, calcium pyrophosphates, hydroxyapatites, trimetaphosphates, insoluble hexametaphosphates and so on in amounts, less than the amount of calcium carbonate, the total amount of abrasive material not being more than 60% by weight of the composition.

Furthermore, the dentifrice formulations may comprise humectants such as glycerol, sorbitol, propyleneglycol, xylitol, lactitol and so on.

Binders and thickeners such as sodium carboxymethylcellulose, xanthan gum, gum arabic etc. may also be included.

Flavours such as peppermint and spearmint oils may also be included, as well as preservatives, opacifying agents, colouring agents, pH-adjusting agents, sweetening agents, teeth whitening agents, peroxy bleaching agents and so on. Stabilising agents for peroxy bleaching agents such as dipicolinic acid or sodium stannate may also be usefully included.

Anti-bacterial agents may also be included such as Triclosan, chlorhexidine, copper-, zinc- and stannous salts such as zinc citrate, sodium zinc citrate and stannous pyrophosphate, sanguinarine extract, metronidazole. Further examples of anti-bacterial agents are quaternary ammonium compounds such as cetylpyridinium chloride; bis-guanides such as chlorhexidine digluconate, hexetidine, octenidine, alexidine; halogenated bisphenolic compounds such as 2,2' methylenebis-(4-chloro-6-bromophenol).

Polymeric compounds which can enhance the delivery of active ingredients such as anti-bacterial agents can also be included. Examples of such polymers are copolymers of polyvinylmethylether with maleic anhydride and other similar delivery enhancing polymers, e.g. those described in DE-A-3,942,643 (Colgate).

Furthermore anti-inflammatory agents such as ibuprofen, flurbiprofen, aspirin, indomethacin etc. may also be included.

Additional anti-caries agents such as stannous fluoride, aminefluorides, plaque buffers such as urea, calcium lactate, calcium glycerophosphate, strontium polyacrylates may also be included. Other optional ingredients include vitamins such as Vitamin C, and plant extracts. Desensitising agents such as potassium citrate, potassium chloride, potassium tartrate, potassium bicarbonate, potassium oxalate, potassium nitrate as well as strontium salts may also be included.

Buffers and salts to buffer the pH and ionic strength of the compositions may also be included such as mono- or trisodium orthophosphate. Liposomes and other encapsulates may also be used to improve delivery or stability of active ingredients.

Furthermore, the oral compositions may comprise anti-calculus agents such as alkalimetal pyrophosphates, hypophosphite-containing polymers, organic phosphonates, phosphocitrates etc.

In addition, the compositions may comprise functional biomolecules such as bacteriocins, antibodies, enzymes and so on.

Other optional ingredients that may be included are e.g. bleaching agents, e.g. those described in EP-A-0,545,594, effervescing systems such as sodium bicarbonate/citric acid systems, colour change systems, and so on.

The present invention will further be illustrated by way of Example.

EXAMPLE 1

The effect of a fully neutralized polyacrylate on the interaction between particulate calcium carbonate and sodium monofluorophosphate was tested in a model system as follows:

20 g of particulate calcium carbonate (Pacal H) and 0.057 g of sodium monofluorophosphate were dispersed in 25 g demineralized water to which 0.04 g formalin and 27 g sorbitol (70%) was added. A varying amount of an aqueous solution (pH10) of sodium polyacrylate (MW of the polyacrylic acid was 8,000) was added to this dispersion, and the resulting mixture was stored at 37° C. for six days, after which the supernatant was filtered and the amount of sodium monofluorophosphate which remained in solution and the level of free fluoride was measured.

The total fluorine level and the free fluoride ion level were measured by Gas Chromatography and by anion selective electrode analysis respectively.

The following results were obtained:

| Sodium polyacrylate (g, calculated as 100% active material) | Sodium monofluorophosphate remaining in solution (in ppm) after 6 days |
|---|---|
| 0.00000 | 105 |
| 0.03625 | 104 |
| 0.0725 | 126 |
| 0.145 | 120 |
| 0.435 | 122 |
| 0.725 | 128 |

EXAMPLE 2

The following formulation is a toothpaste according to the invention:

|  | % by weight |
|---|---|
| Sorbitol (70%) | 27.00 |
| fine ground natural chalk | 40.00 |
| sodium monofluorophosphate | 1.14 |
| saccharin | 0.20 |
| thickening silica | 2.00 |
| sodium carboxymethylcellulose | 0.90 |
| sodium laurylsulphate | 2.50 |
| sodium polyacrylate (as in Example 1) | 0.75 |
| formalin | 0.04 |
| flavour | 1.10 |
| demineralized water | 24.37 |

EXAMPLE 3

Formulations according to Example 2 were made, but with varying amounts of the sodium polyacrylate (0.25%, 0.75% and 1.30%). A control formulation without sodium polyacrylate was also made, as well as a comparative formulation without sodium polyacrylate, containing 0.5% trisodium orthophosphate and 0.5% monosodium orthophosphate. These formulations were stored for 3 months at 20° C. and 40° C. The pH was measured (5 g paste in 20 g distilled water; stiring for 10 minutes and then measuring the pH), and the amount of extractable F was determined as in Example 1. The following results were obtained.

| Formulation | pH (at 20° C.) | ppm extractable F (at 40° C.) |
|---|---|---|
| Comparative | 8.99 | 388 |
| 0%    Na-polyacrylate (control) | 8.27 | 944 |

-continued

| Formulation | | pH (at 20° C.) | ppm extractable F (at 40° C.) |
|---|---|---|---|
| 0.25% | " | 8.53 | 1081 |
| 0.75% | " | 8.92 | 1088 |
| 1.30% | " | 9.12 | 1152 |

What is claimed is:

1. An oral care composition comprising particulate calcium carbonate having an average particle size between 1 and 60 μm as a major abrasive cleaning agent, and a fluorine-providing compound as anti-caries agent, wherein the composition has a pH of above 8.5 and further comprises a fully neutralized polyacrylic acid having a molecular weight between 1000 and 250,000.

2. A composition according to claim 1, wherein the molecular weight is between 2500 and 100,000.

3. A composition according to claim 2, wherein the molecular weight is between 4000 and 70,000.

4. A composition according to claim 1, wherein the polyacrylic acid is fully neutralized with an alkalimetal-, ammonium-, or (alkylol) amine compound.

5. A composition according to claim 4, wherein the fully neutrlized polyacrylic acid is sodium polyacrylate.

6. A composition according to claim 1, wherein the fully neutralized polyacrylic acid is present in the composition in an amount of from 0.05–5% by weight of the composition.

7. A composition according to claim 6, wherein the amount is from 0.1–3% by weight of the composition.

* * * * *